United States Patent
Kim

(10) Patent No.: US 7,323,196 B2
(45) Date of Patent: Jan. 29, 2008

(54) PHARMACEUTICAL COMPOSITION COMPRISING EXTRACTS OF RADIX CLEMATIDIS FOR TREATING AND PREVENTING DIABETES, DIABETIC COMPLICATIONS, INSULIN RESISTANCE AND INSULIN RESISTANCE SYNDROME

(76) Inventor: Sung-Jin Kim, 104-2003 Hanshin Apt. 60, Chungryangri-dong, Dongdaemun-gu, Seoul (KR)

( * ) Notice: Subject to any disclaimer, the term of this patent is extended or adjusted under 35 U.S.C. 154(b) by 0 days.

(21) Appl. No.: 11/282,529

(22) Filed: Nov. 18, 2005

(65) Prior Publication Data

US 2006/0110480 A1 May 25, 2006

(30) Foreign Application Priority Data

Nov. 22, 2004 (KR) ...................... 10-2004-0095806

(51) Int. Cl.
*A61K 36/716* (2006.01)
(52) U.S. Cl. ...................... 424/725; 424/773
(58) Field of Classification Search ...................... None
See application file for complete search history.

(56) References Cited

U.S. PATENT DOCUMENTS 5,910,307 A * 6/1999 Kwak et al. ................ 424/745

6,071,521 A * 6/2000 Kim ........................... 424/728

FOREIGN PATENT DOCUMENTS

CN 1513506 A * 7/2004
JP 44000237 B4 * 1/1969

OTHER PUBLICATIONS www.diabetes.org/diabetes-prevention/how-to-prevent-diabetes.jsp—accessed May 24, 2006.*
English translation of CN 1513506.*

* cited by examiner

*Primary Examiner*—Susan Coe Hoffman
(74) *Attorney, Agent, or Firm*—Stetina Brunda Garred & Brucker

(57) ABSTRACT

Disclosed is a composition comprising extracts of Radix *Clematidis* for preventing and treating diabetes, diabetic complications, insulin resistance and insulin resistance syndrome. The composition of the present invention for preventing and treating diabetes, diabetic complications, insulin resistance and insulin resistance syndrome, comprises extracts of Radix *Clematidis* in an amount of 0.5-50 wt % based on the total composition weight.

10 Claims, 3 Drawing Sheets

Oral Glucose tolerance Test

Liver in a mouse

IP: anti-IR
Blot: anti-pTyr

← IR β-subunit

Water Extract   MeOH Extract   Control

PHARMACEUTICAL COMPOSITION COMPRISING EXTRACTS OF RADIX CLEMATIDIS FOR TREATING AND PREVENTING DIABETES, DIABETIC COMPLICATIONS, INSULIN RESISTANCE AND INSULIN RESISTANCE SYNDROME

CROSS-REFERENCE TO RELATED APPLICATIONS

This application claims benefit under 35 U.S.C. § 119 from Korean Patent Application No. 2004-95806, filed on Nov. 22, 2004, the entire content of which is incorporated herein by reference.

BACKGROUND OF THE INVENTION

1. Field of the Invention

The present invention relates to a pharmaceutical composition comprising extracts of Radix *Clematidis* for treating and preventing diabetes, diabetic complications, insulin resistance and insulin resistance syndrome.

2. Description of the Related Art

Diabetes mellitus is a severe chronic metabolic abnormality. There were 194 million diabetic patients and more than 300 million people exposed to a risk of developing diabetes around the world in the year 2003. WHO predicted that the diabetic population would increase to 333 million by 2025 (Yakup Daily, Aug. 28, 2003). About 90% of diabetic patients have type II diabetes mellitus (World Health Organization website, Fact sheet 236, 1999; Accessed Jul. 25, 2002). It is assumed that the annual costs needed for treating diabetic patients aged between 20 and 79 amount to a minimum of 153 billion dollars. It is expected that these medical expenses will reach from 213 billion to 396 billion dollars in 2025. Considering that enormous medical expenses are spent and many people are exposed to diabetes, the development of drugs for preventing and treating diabetes and diabetic complications is in urgent need.

Type I diabetes mellitus is an immune-mediated disease caused by chronically and selectively destroyed pancreatic β-cells. As a consequence, a destruction of β-cells secreting insulin results in insulin deficiency that leads to hyperglycemia, diabetes, polydipsia and weight loss, and so on. Diabetic complications are loss of eyesight, renal failure, neurological disorders, heart disease, etc.

In case of type II diabetes mellitus, the first shown dysfunction is insulin resistance that insulin-sensitive cells do not respond to insulin of normal level (Consensus Development conference on Insulin Resistance 5-6 Nov. 1997, American Diabetes Association, Diabetes Care, 1998; 21:310-314). Pancreatic β-cells increase insulin secretion in order to overcome such insulin resistance. But, as time passes, β-cell function lowers, consequently insulin secretion decreases, resulting in a hyperglycemia. Type II diabetes mellitus is complexly caused by insulin-mediated suppression dysfunction of hepatic glucose excretion, insulin-mediated glucose uptake disorders into muscle and adipose cells, and β-cell dysfuction (DeFronzo R A, Bonadonna R C, Ferrannini E, Pathogenesis of NIDDM, A balanced overview, Diabetes Care, 1992; 15: 318-368). And, this insulin resistance is an important cause in the development of various metabolic diseases. Insulin resistance indicates that a tissue response to insulin actions decreases, and the resultant symptoms are called insulin resistance syndrome (IRS), syndrome X, metabolic syndrome, plurimetabolic syndrome, new world syndrome, syndrome X+, deadly quartet, or diabesity (Zimmet, P. Addressing the insulin resistance syndrome. A role for the thiazolidinediones, 2002). Insulin resistance is accompanied with insulin-mediated glucose uptake disorders, glucose intolerance, hyperinsulinemia, triglyceride (very low density lipoprotein triglyceride) increase, HDL cholesterol decrease, hypertension, and so on (Reaven, G. M. Banting lecture. Role of insulin resistance in human disease. Diabetes 37, 1595-1607, 1988). Insulin resistance syndrome contains systemic obesity, central obesity, upper abdominal obesity, arteriosclerosis, acanthosis nigricans, polycystic ovarian syndrome, hyperuricemia, PAI-1 (plasminogen activator inhibitor-1) increase, thrombolystic abnormality, endothelial and smooth muscle dysfunction, microalbuminuria, and so on (Peter, P., Nuttall, S. L., Kendall, M. J. Insulin resistance—the new goal!. J. Clinical Pharmacy and Therapeutics 28, 167-174, 2003). According to a recent study, it is suggested that insulin resistance cause the following diseases: sleep apnoea (Punjabi, N. M., Ahmed, M. M., Polotsky, V. Y., Reamer, B. A., O'Donnell, C. P. Sleep-disordered breathing, glucose intolerance, and insulin resistance. Respiratory Physiology & Neurobiology 136, 167-178, 2003); prostate cancer (Barnard, R. J., Aronson, W. J., Tymchuk, C. N., Ngo, T. H. Prostate cancer: another aspect of the insulin-resistance syndrome, Obesity reviews 3, 303-308, 2002); type I diabetes (Greenbaum, C. J. Insulin resistance in type 1 diabetes. Diabetes Metab. Res. Rev. 18, 192-200, 2003); affective disorders (Rasgon, N., Jarvik, L. Insulin resistance, affective disorders, and Alzheimer's disease: review and hypothesis. J. Gerontol. A Biol. Sci. Med. Sci. 59, 178-183, 2004); Alzheimer's disease (Watson, G. S., Craft, S. The role of insulin resistance in the pathogenesis of Alzheimer's disease: implications for treatment. CNS Drugs. 17, 27-45, 2003); stroke (Kernan, W. N., Inzucchi, S. E., Viscoli, C. M., Brass, L. M., Bravata, D. M., Horwits, R. I. Insulin resistance and risk for stroke. Neurology 59, 809-815, 2002); breast cancer (Stoll, B. A. Upper abdominal obesity, insulin resistance and breast cancer risk. Int. J. Obes. Relat. Metab. Disord. 26, 747-753, 2002); inflammation (Perseghin, G., Petersen, K., Shulman, G. I. Cellular mechanism of insulin resistance: potential links with inflammation. Int. J. Obes. Relat. Metab. Disord. 27 Suppl. 3, S6-S11, 2003); rheumatoid arthristis (Dessein, P. H., Joffe, B. I., Stanwix, A. E. Inflammation, insulin resistance, and aberrant lipid metabolism as cardiovascular factors in rheumatoid arthristis. J. Rheumatol. 30, 1403-1405, 2003); etc. Accordingly, a substance capable of preventing and treating insulin resistance can be used as medicament for preventing and treating the above insulin resistance syndrome.

SUMMARY OF THE INVENTION

An object of the present invention is to provide a pharmaceutical composition comprising extracts of Radix *Clematidis* for treating and preventing diabetes, diabetic complications, insulin resistance and insulin resistance syndrome, which is safe without toxicity.

BRIEF DESCRIPTION OF THE DRAWINGS

The above aspects and features of the present invention will be more apparent by describing certain embodiments of the present invention with reference to the accompanying drawings, in which.

DETAILED DESCRIPTION OF THE PREFERRED EMBODIMENTS

Figure 1:
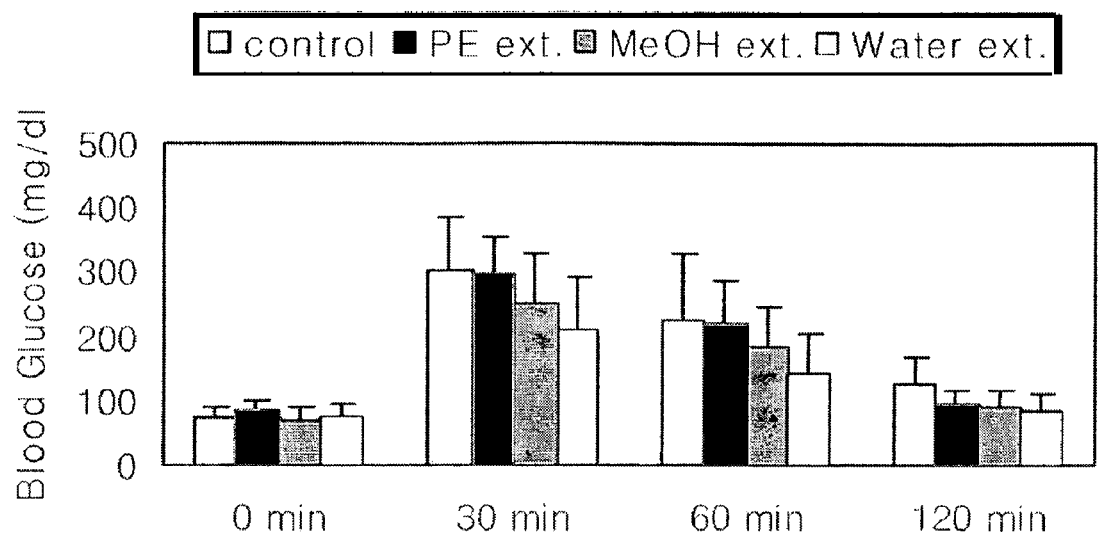
FIG. 1 illustrates a blood glucose lowering effect of extracts of Radix *Clematidis*. The value is an average±standard deviation (n=5).
Figure 2:
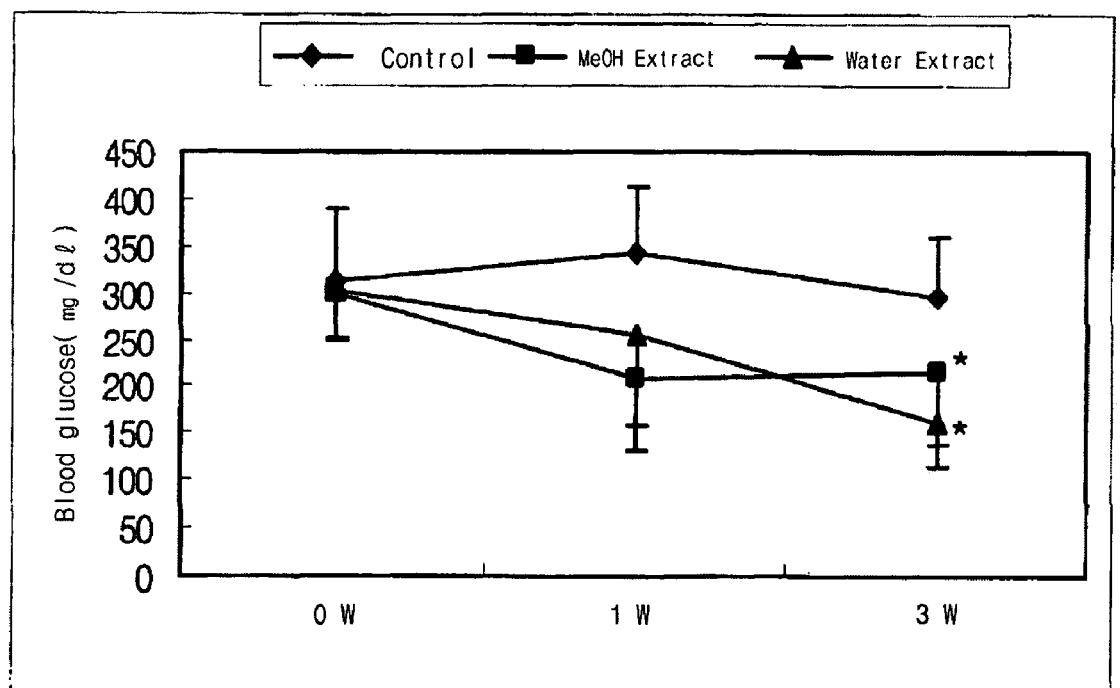
FIG. 2 illustrates a blood glucose lowering effect of extracts of Radix *Clematidis*. The value is an average±standard deviation (n=5) and significance to a control group is *: P<0.05.
Figure 3:
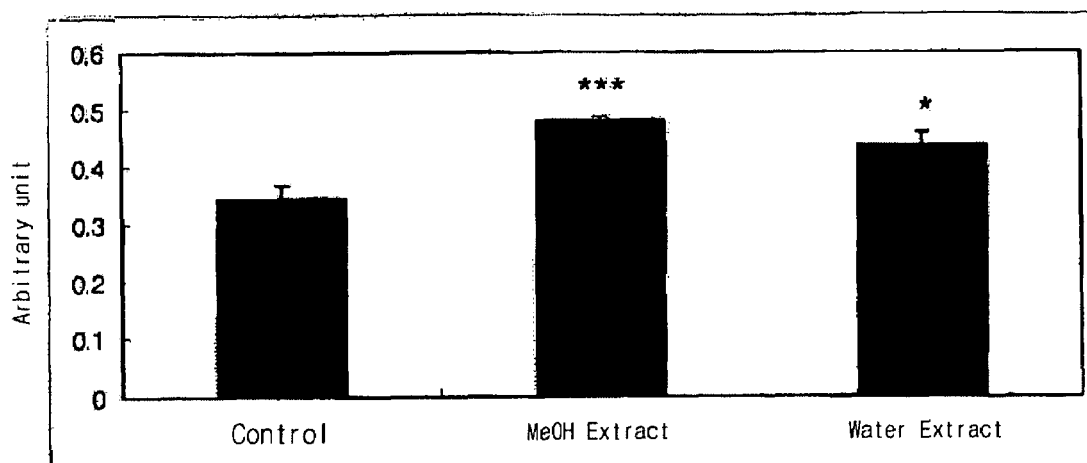
FIG. 3 illustrates a glycogenesis improvement effect of extracts of Radix *Clematidis*. The value is an average±standard deviation (n=5) and significance to a control group is *: P<0.05 and **: P<0.001.
Figure 4:
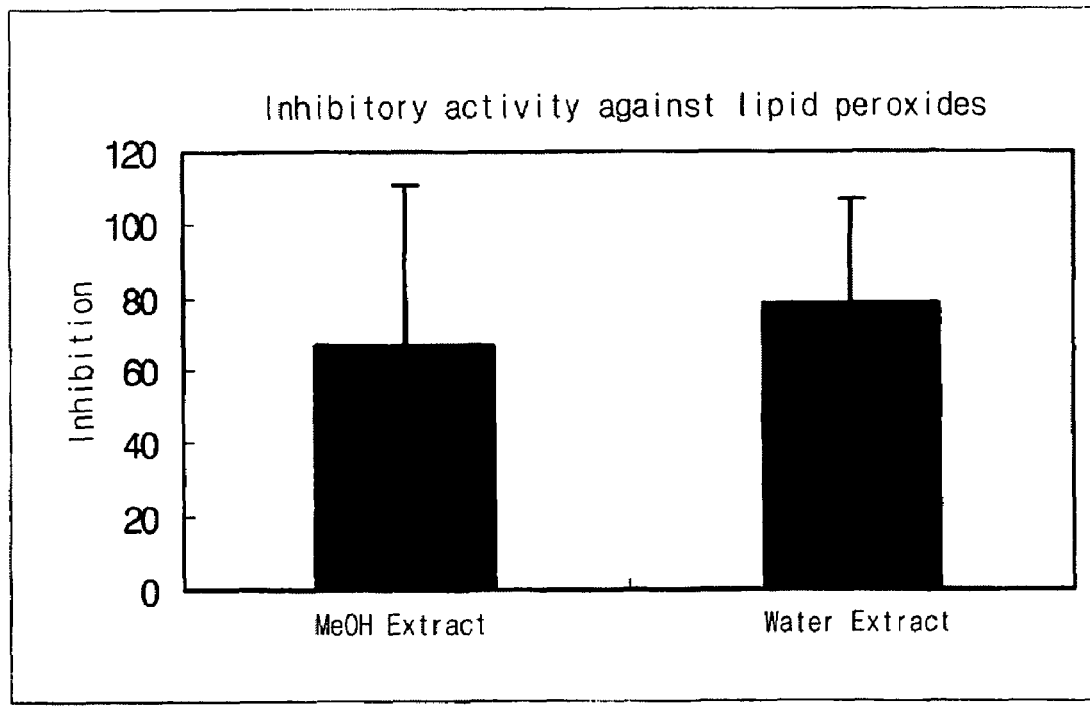
FIG. 4 illustrates an inhibitory activity effect against lipid peroxide of extracts of Radix *Clematidis*. The value is an average±standard deviation (n=5).
Figure 5:
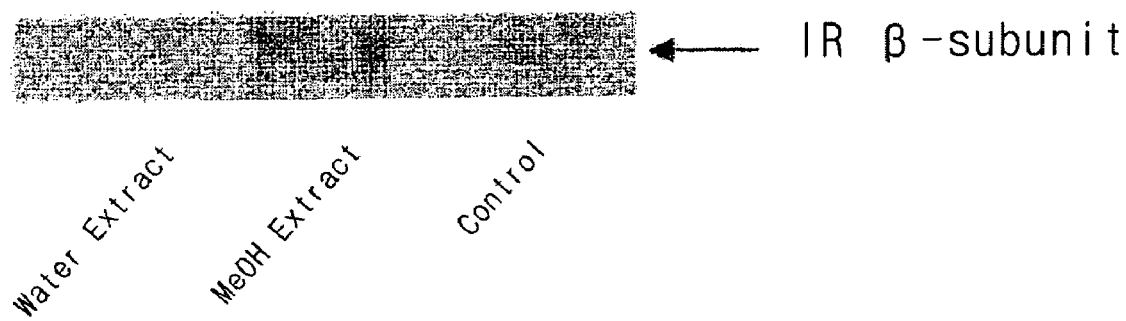
FIG. 5 shows a insulin receptor activity improvement effect of extracts of Radix *Clematidis*.
Figure 6:
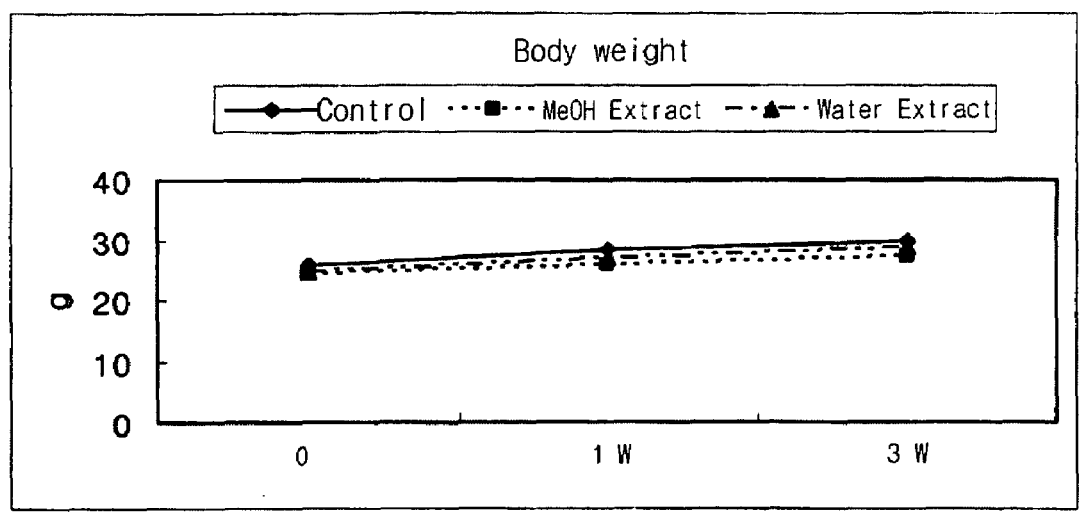
FIG. 6 illustrates an effect of extracts of Radix *Clematidis* on body weight. The value is an average±standard deviation (n=5).

Radix *Clematidis* is dry roots and rhizomes of perennial and deciduous plants in the Ranunculaceae, such as *Clematis mandshurica* (*Clematis mandshurica* MAXIM., *Clematis mandshurica* RUPR.), *Clematis brachyura* MAXIM., *Clematis paniculata* THUNB., *Clematis florida* THUNB., *Clematis patens* MORREN. and related plants in the same genus and also includes *Clematis chinensis* OSBECK. and *Clematis hexapetala* PALL. in china. It is known to have pharmacological actions such as analgesic action, antimalarial action, antibacterial action, abortive action, biliary excretion enhancement, smooth muscle relaxation, antidiuretic action, cardiotonic action, hypotensive action, and so on (Chinese Materia Medica, Chemistry, Pharmacology and Application, You-Ping Zhu, 1998). Components in Radix *Clematidis* are anemonin, oleanolic acid, quinatoside A, 3-0-[β-D-xylopyranosyl-(1-3)-α-L-ramnopyranosyl-(1-2)-α-L-arabinopyrano]oleanolic acid, 3-0-[β-D-ribopyranosyl-(1-3)-α-L-ramnopyranosyl-(1-2)-α-L-arabinopyrano]oleanolic acid, *Clematis chinensis* Saponin CP2a, *Clematis chinensis* Saponin CP0, *Clematis chinensis Saponin* CP3a, *Clematis chinensis* Prosapogenin Cp10a, *Clematis chinensis* Prosapogenin Cp9a, *Clematis chinensis* Prosapogenin Cp7a, *Clematis chinensis* Prosapogenin Cp8a, *Clematis chinensis* Prosapogenin CP-10, *Clematis chinensis* Prosapogenin CP-9, *Clematis chinensis* Prosapogenin CP2b, *Clematis chinensis* Prosapogenin CP3b, saponin clematoside A, A', B, C and etc (TradiMed Database 1996, Natural Products Research Institute). But, it has not been reported that Radix *Clematidis* has an effect on diabetes, diabetic complications, and insulin resistance.

As a result of making an effort to discover substances for preventing and treating diabetes and diabetic complications from herbal medicine, we have found that extracts of Radix *Clematidis* have a blood glucose lowering action, diabetic inhibitory action, glycogenesis enhancement, activity enhancement of insulin receptors, and inhibitory effect against lipid peroxidation, and can be used as a medicament for preventing and treating diabetes (type I and type II), diabetic complications, insulin resistance and insulin resistance syndrome.

The extracts of Radix *Clematidis* of the present invention can be prepared according to the following method.

The first extraction: extracts of Radix *Clematidis* can be obtained by extracting Radix *Clematidis* with solvent selected from a group consisting of petroleum ether, benzene, n-hexane, toluene and heptane using a reflux condensation or ultrasonic waves. At this time, a extraction temperature is in a range of 5 to 80° C., preferably 30 to 55° C., and a extraction time is in a range of 15 minutes to 48 hours, preferably 30 minutes to 12 hours. In addition, it can be obtained by extracting Radix *Clematidis* with solvent selected from the above solvent group through a supercritical fluid extraction.

The second extraction: a soluble fraction can be obtained by adding to the residues of Radix *Clematidis* from the first extraction solvent selected from a group consisting of C1-4 lower alcohol, a mixture of the lower alcohol and water, acetone, chloroform, methylene chloride, ether, and ethylacetate using a reflux condensation or ultrasonic waves. At this time, a reaction temperature is in a range of 5 to 80° C., preferably 30 to 55° C., and a reaction time is in a range of 15 minutes to 48 hours, preferably 30 minutes to 12 hours. In addition, it can be obtained by extracting the residues of Radix *Clematidis* with solvent selected from the above solvent group through a supercritical fluid extraction.

The third extraction: a water soluble fraction can be obtained by adding water to the residues of Radix *Clematidis* from the second extraction using a reflux condensation or ultrasonic waves. At this time, a reaction temperature is in a range of 5 to 80° C., preferably 30 to 55° C., and a reaction time is in a range of 15 minutes to 48 hours, preferably 30 minutes to 12 hours. It can be obtained by extracting the residues of Radix *Clematidis* with solvent selected from the above solvent group through a supercritical fluid extraction.

In addition, an additional fractional process by pH control can be performed on the extracts of Radix *Clematidis* by a general practionation: a chloroform soluble fraction can be obtained by adjusting extracts of Radix *Clematidis* to pH 2-4 with acid to be further extracted with an equal amount of chloroform. And, a chloroform insoluble fraction can be adjusted to pH 9-12 with ammonium hydroxide and extracted with an equal amount of a chloroform-methanol mixture, wherein a chloroform-methanol insoluble fraction was further extracted with methanol and fractionated to obtain a methanol soluble fraction and a water fraction that is not soluble in methanol. Then, a mixing ratio of chloroform:methanol is preferably in a range of 1:0.1-1 (Harborne J. B. Phytochemical methods: *A guide to modern techniques of plant analysis*. 3rd Ed. pp 6-7, 1998).

A composition containing the extracts of Radix *Clematidis* of the present invention can further comprise pharmaceutically acceptable carriers and more than one ingredient selected from a group consisting of additives.

Carriers that can be included in a composition containing the extracts of Radix *Clematidis* of the present invention generally comprise materials referred to as excipients or diluents. Carriers are more than one ingredient selected from a group consisting of lactose, dextrose, sucrose, sorbitol, mannitol, xylitol, erythritol, maltitol, starch, isomerized sugar, white sugar, acacia gum, alginate, gelatin, calcium, phosphate, calcium silicate, cellulose, methyl cellulose, microcrystalline cellulose, polyvinyl pyrrolidone, water, methylhydroxybenzoate, propylhydroxybenzoate, para-oxybenzoate, methyl para-oxybenzoate, para-oxypropylbenzoate, talc, magnesium stearate and mineral oils.

Furthermore, additives that can be included in a composition containing the extracts of Radix *Clematidis* of the present invention are more than one ingredient selected from a group consisting of natural carbohydrates, savoring agents, nutrients, vitamin, mineral (electrolyte), flavoring agents (synthetic and natural flavoring agent), colorant, filler (cheese, chocolate, etc), pectic acid and its salts, alginic acid and its salts, organic acid, protective colloidal thickener, pH modifier, stabilizer, antiseptic, antioxidant, glycerin, alcohol, carbonating agent, and pulp.

The composition containing the extracts of Radix *Clematidis* according to the present invention can be formulated in a form of oral formulations such as powder, tablet, capsule, suspension, emulsion, syrup, aerosol, etc; external application; suppository or sterile injection according to a general method, respectively.

A daily dose of extracts of Radix *Clematidis* can vary with patient's age, sex, and weight, and may be administered in a dose of 0.1 to 500 mg/kg once or several times a day. In addition, a dosage of extracts and fractions of Radix *Clematidis* can be increased and decreased depending on administration routes, disease severity, sex, weight, age and so on. The above dosage is not intended to limit the scope of the invention in any way. The extracts of Radix *Clematidis* of the present invention scarcely have toxicity and side effects, therefore can be safely used even in taking it for a long time for the purpose of prevention.

The above extracts of Radix *Clematidis* of the present invention also can be used in various foods, beverages, gum, tea, vitamin complex supplements, and foods and beverages like health care foods together with sitologically acceptable additives.

In foods containing the extracts of Radix *Clematidis* of the present invention, the extracts of Radix *Clematidis* can be used in an amount of 0.1 to 15 wt %, preferably 1 to 10 wt % relative to total food weight.

Furthermore, in beverages containing the extracts of Radix *Clematidis* of the present invention, the extracts of Radix *Clematidis* may be added in a ratio of 1-30 g, preferably 3-10 g based on beverage 100 ml.

Moreover, sitologically acceptable additives that can be contained in the foods and beverages according to the present invention are more than one ingredient selected from a group consisting of natural carbohydrates, savoring agents, nutrients, vitamin, mineral (electrolyte), flavoring agents (synthetic and natural flavoring agent), colorant, filler (cheese, chocolate, etc), pectic acid and its salts, alginic acid and its salts, organic acid, protective colloidal thickener, pH modifier, stabilizer, antiseptic, antioxidant, glycerin, alcohol, carbonating agent, and pulp.

The above additives are preferably added in a range of 0.01-25 parts by weight per 100 parts by weight of the food or beverage composition.

In addition, natural carbohydrates such as monosaccharides (glucose and fructose), disaccharides (maltose and sucrose) and polysaccharides (dextrin and cyclodextrin); and sugar alcohols such as xylitol, sorbitol, erythritol, etc can be used and are preferably added in an amount of about 1-20 g, preferably about 5-12 g per beverage composition 100 ml.

Natural savoring agents such as thaumatin, stevia extracts (for example, revaudioside A, glycyrrhizin, etc); and synthetic savoring agents such as saccharins and aspartame, etc can be used as a savoring agent.

The beverage composition of the present invention puts no special limitation on liquid ingredients except that it contains the above extracts of Radix *Clematidis* as an essential ingredient in the indicated ratio.

Hereinafter, the preparative examples illustrate the invention in more detail, but the present invention is not to be limited to these examples.

EXPERIMENTAL EXAMPLE 1

Preparation of Extracts of Radix *Clematidis*

1) Method

Radix *Clematidis* (500 g) was finely cut, prior to adding thereto a five-fold volume of petroleum ether (2,500 ml) to be extracted using a reflux condenser, repeating the process three times, concentrating the petroleum ether extracts using a rotary evaporator, and lyophilizing the concentrates to obtain an extract 0.36 g. MeOH 2,500 ml was added to the residues to be extracted using a reflux condenser, prior to repeating the process three times, concentrating the MeOH extracts using a rotary evaporator, and lyophilizing the MeOH concentrates to obtain an extract 29.18 g. $H_2O$ 2,500 ml was added to the residues to be extracted using a reflux condenser, prior to repeating the process three times, concentrating the water extracts using a rotary evaporator, and lyophilizing the MeOH concentrates to obtain an extract 46.46 g.

EXPERIMENTAL EXAMPLE 2

Oral Glucose Tolerance Test

1) Method

A mouse was starved for 18 hours, prior to orally administering a medicament to the mouse in a dose of 80 mg/kg. After an hour passed, glucose of 2 g/kg was orally administered to measure blood glucose level in 30, 60, and 120 minutes using a blood glucose testing kit.

2) Result

MeOH extracts and water extracts of Radix *Clematidis* induced a blood glucose lowering effect from 30 minutes to 120 minutes after administering glucose. Petroleum ether extracts of Radix *Clematidis* showed no change in 30 minutes after administering glucose but induced a blood glucose lowering effect from 60 minutes to 120 minutes, as compared with that of a control group.

EXPERIMENTAL EXAMPLE 3

Blood Glucose Lowering Effect Using a Streptozotocin-Induced Diabetic Mouse

1) Method

A mouse was used two weeks after streptozotocin (50 mM citrate buffer, pH 4.5) was intraperitoneally administered to the mouse (J Gene Med. 2003, 5, 417-424). Extracts of Radix *Clematidis* were orally administered in a dose of 80 mg/kg once a day for 5 days a week and given for 4 consecutive weeks. The change of blood glucose level was measured once a week.

2) Result

In case of a control group without administering extracts of Radix *Clematidis*, the blood glucose level was 313 mg/dl, 343.75 mg/dl after a week and 294.25 mg/dl after 3 weeks, consequently hyperglycemia was maintained. However, in case of an administered group with MeOH extracts of Radix *Clematidis*, blood glucose level was 297.83 mg/dl just before an administration but 209.33 mg/dl a week after an administration, and decreased by about 30% compared with that prior to an administration. Furthermore, when MeOH extracts of Radix *Clematidis* were administered for 3 consecutive weeks, blood glucose level was 214 mg/dl and kept in a low state. In case of an administered group with the MeOH extract, blood glucose level was 302.5 mg/dl just before an administration but 253.66 mg/dl a week after an administration, and decreased by about 16% compared with that prior to an administration. In addition, when water extracts of Radix *Clematidis* were administered for 3 consecutive weeks, blood glucose level was 162 mg/dl and decreased by 46% as compared with that prior to an administration.

EXPERIMENTAL EXAMPLE 4

Measurement of Glycogenesis Ability

1) Method

Hepatocyte was dissolved in 0.1% sodium lauryl sulfates 24 hours after HepG2 hepatocyte was treated with extracts of Radix *Clematidis* in a dose of 10 µg/ml. Thereto, ethanol was added to precipitate glycogen. The precipitated glycogen was dissolved in conc. sulfuric acid. Glucose produced was reacted with phenol to obtain a stained product. An absorbance of the stained product was measured at 490 nm (J Applied Physiol, 1970, 28, 234-236).

2) Result

In case of an administered group with MeOH extracts, glycogenesis ability increased by 38% compared with that of a control group. The glycogenesis ability of an administered group with a water extract increased by 27% compared with that of a control group.

EXPERIMENTAL EXAMPLE 5

Measurement of Lipid Peroxide (TBARS)

1) Method

1. Isolation of Microsome (Hogebuoom G. H. 1965. General methods for the isolation of liver cell components: Fraction of cell components of animal tissues. Method Enzymol. 1: 16-19)

An avulsed liver from a mouse was washed with saline and finely cut with a scissor, prior to adding thereto 0.25M sucrose solution (0.25M sucrose/5 mM Tris-HCl, pH 7.4/0.1 mM EDTA) of an 8-fold volume of liver weight to be ground with a tissumizer. The ground hepatic solution was centrifuged at 7,000×g for 10 minutes to obtain a supernatant. The supernatant was ultracentrifuged at 77,000×g for 60 minutes to obtain a precipitate. The precipitate was washed with 5 mM Tris-HCl, pH 7.4 buffer three times to obtain a final precipitate. The final precipitate was diluted with 5 mM Tris-HCl, pH 7.4 buffer and preserved at −20° C.

2. Measurement of Inhibitory Activity Against Lipid Peroxidation (Ohakawa H, Ohishi N, Yagi K. Assay for lipid peroxides in animal tissues by thiobarbituric acid reaction. Anal. Biochem. 95, 351-358, 1979)

A 100 mM Tris-HCl buffer, pH 7.5, 4 mM $FeSO_4.7H_2O$ and extracts of Radix *Clematidis* (10 µg/ml) were added to the isolated microsome, prior to adjusting the mixture to pH 7.4, and adding thereto 2 mM ascorbic acid to be reacted at 37° C. for 60 minutes. And then, a mixture of TCA (3 M)-HCl (2N) (1:1) was added to stop the reaction, centrifuged at 3,500×g for 10 minutes to mix the supernatant with 0.67% TBA solution, and boiled at 100° C. for 20 minutes. An absorbance was measured at 530 nm to calculate an inhibitory activity against lipid peroxidation.

2) Result

An administered group with MeOH extracts of Radix *Clematidis* showed an inhibitory rate against lipid peroxide formation of 66.7% and an administered group with water extracts induced an inhibitory rate against lipid peroxide formation of 77.9%, as compared with a control group.

EXPERIMENTAL EXAMPLE 6

Measurement of Phosphorylation of Insulin Receptor Tylosin Residues

1) Method

1. Preparation of Hepatic Lysate

Extracts of Radix *Clematidis* were orally administered to a male IC mouse starved for 16 hours in a dose of 80 mg/kg. After an hour passed, the mouse was dissected to separate a liver at 4° C. Hepatic homogenization was provided by a little modification of a conventional method (Zhao, H., Xu, H., Moore, E., Meiri, N., Quon, M. J., Alkon, D., L., Insulin receptors and spatial memory. J. Biol. Chem. 274, 34893-34902, 1999). The separated liver again was suspended in a buffer A containing 50 mM Tris HCl, pH 7.4, 1 mM EDTA, 1 mM EGTA, 150 mM NaCl, 1% Triton X-100, 0.5 mM PMSF, 1 mM Na3VO4, leupeptin and aprotinin 1 µg/ml, and homogenized using a Potter-Elvehjem homogenizer. The lysate was rotated at 10,000×g for 20 minutes. The supernatant was analyzed on proteins and preserved at −70° C.

2. Immunoprecipitation

An immunoprecipitation was carried out by a known technique (Kim S. J., Kahn, C. R. Insulin stimulates phosphorylation of c-Jun, c-Fos and Fos-related proteins in cultured adipocytesd. J. Biol. Chem. 269, 11887-11892, 1994). An equal amount of proteins from hepatic lysate were cultured with an insulin receptor antibody at 4° C. for an hour, followed by adding protein A-cephalos to precipitate the immune complex by a centrifuge. The pellets were continuously washed with buffer A (0.01M Tris, pH 7.4, 1M NaCl, 1% Nonidet P-40), buffer B (0.01M Tris, pH 7.4, 0.1M NaCl, 0.01M EDTA, 1% Nonidet P-40, 0.3% SDS) and buffer C (0.01M Tris, pH 7.4 and 1% Nonidet P-40) 1 ml. The final pellets were dissolved in a Laemmli buffer containing dithiothreitol 100 mM, boiled for 5 minutes, and centrifuged with a microcentrifuge, followed by performing SDS-PAGE with the supernatant and analyzing western blots using anti-pTyr antibody.

3. Western Blot Analysis

An equal amount of hepatic proteins were applied to SDS polyacrylamide gel. An electric transfer of proteins from gels to nitrocellulose sheets (Scheleicher and Schuell) was carried out at 100V (constant voltage) for an hour as described by Towbin et al (Towbin H., Staehelin, J., Gordon, J. Electric transfer of proteins from polyacrylamide gels to nitrocellulose sheets: procedure and some applications. Proc. Natl. Acad. Sci. USA 76, 4350-4354, 1979). The filter papers were probed with PBS containing 0.1% Tween 20 and 3% bovine serum albumin at 23° C. for an hour. And then, the blots were cultured with HRP conjugate anti-rabbit IgG for 30 minutes and five times washed with PBS containing Tween 20 for 10 minutes, respectively. And, the detection for fixed specific antigen was performed by ECL (NEN).

2) Result

An administered group with MeOH extracts of Radix *Clematidis* induced the noticeable tylosin phosphorylation of insulin receptors compared with a control group. This suggests that extracts of Radix *Clematidis* remarkably stimulate the activities of insulin receptors.

EXPERIMENTAL EXAMPLE 7

Measurement of Body Weight

1) Method

Change of body weight was measured every week before and after extracts of Radix *Clematidis* (80 mg/kg, PO) were administered.

2) Result

A group taking extracts of Radix *Clematidis* for 3 weeks showed no significant difference in change of body weight compare with a control group without extracts of Radix *Clematidis*. This result proves that even if extracts of Radix *Clematidis* are administered for a long time, change of body weight is not caused.

EXPERIMENTAL EXAMPLE 8

Measurement of Lethal Dose 50%

1) Method

The number of dead animal was counted after extracts of Radix *Clematidis* were orally administered to 10 mice per a dose in a dose of 50 mg/kg, 500 mg/kg, and 5000 mg/kg.

2) Result

Even if extracts of Radix *Clematidis* were administered in a dose of 50 mg/kg, 500 mg/kg, and 5000 mg/kg, no mouse was dead. Consequently, LD 50 is considered to be more than 5 g/kg.

PREPARATIVE EXAMPLE 1

Tablet

According to the following composition, tablets were prepared by a general preparation.

1-1. Tablet Composition

| | |
|---|---|
| Petroleum ether extracts of Radix Clematidis | 500.0 mg |
| Lactose | 500.0 mg |
| Talc | 5.0 mg |
| Magnesium stearate | 1.0 mg |

1-2. Tablet Composition

| | |
|---|---|
| Methanol extracts of Radix Clematidis | 50.0 mg |
| Lactose | 50.0 mg |
| Talc | 0.5 mg |
| Magnesium stearate | 0.1 mg |

1-3. Tablet Composition

| | |
|---|---|
| Water extracts of Radix Clematidis | 50.0 mg |
| Lactose | 50.0 mg |
| Talc | 0.5 mg |
| Magnesium stearate | 0.1 mg |

PREPARATIVE EXAMPLE 2

Capsule

According to the following composition, capsules were prepared by the following method. Extracts of Radix *Clematidis* were screened and mixed with excipients, prior to filling capsules with the mixture to prepare capsules.

2-1. Capsule Composition

| | |
|---|---|
| Petroleum ether extracts of Radix Clematidis | 500.0 mg |
| Starch 1500 | 10.0 mg |
| Magnesium stearate BP | 100.0 mg |

2-2. Capsule Composition

| | |
|---|---|
| Methanol extracts of Radix Clematidis | 50.0 mg |
| Starch 1500 | 1.0 mg |
| Magnesium stearate BP | 10.0 mg |

2-3. Capsule Composition

| | |
|---|---|
| Water extracts of Radix Clematidis | 50.0 mg |
| Starch 1500 | 1.0 mg |
| Magnesium stearate BP | 10.0 mg |

PREPARATIVE EXAMPLE 3

Syrup

According to the following composition, syrup was prepared by the following method. First, white sugar was dissolved in purified water, prior to adding thereto para-oxybenzoate, para-oxypropylbenzoate and extracts of Radix *Clematidis* to be dissolved at 60° C. and cooled. Thereto, purified water was added to make up to 150 ml.

3-1. Syrup Composition

| | |
|---|---|
| Petroleum ether extracts of Radix Clematidis | 5.0 g |
| White sugar | 95.1 g |
| Para-oxybenzoate | 80.0 mg |
| Para-oxypropylbenzoate | 16.0 mg |

Add purified water to make the total volume up to 150 ml.

3-2. Syrup Composition

| | |
|---|---|
| Methanol extracts of Radix Clematidis | 50.0 mg |
| White sugar | 95.1 g |
| Para-oxybenzoate | 80.0 mg |
| Para-oxypropylbenzoate | 16.0 mg |

Add purified water to make the total volume up to 150 ml.

3-3. Syrup Composition

| | |
|---|---|
| Water extracts of Radix Clematidis | 50.0 mg |
| White sugar | 95.1 g |

-continued

| | |
|---|---|
| Para-oxybenzoate | 80.0 mg |
| Para-oxypropylbenzoate | 16.0 mg |

Add purified water to make the total volume up to 150 ml.

PREPARATIVE EXAMPLE 4

Solution

The following ingredients were formulated by a general solution preparation, prior to filling brown bottles to make solution.

4-1. Solution Composition

| | |
|---|---|
| Petroleum ether extracts of Radix Clematidis | 500.0 mg |
| Isomerized sugar | 20.0 g |
| Antioxidant | 5.0 mg |
| Methyl para-oxybenzoate | 2.0 mg |

Add purified water to make the total volume up to 100.0 ml.

4-2. Solution Composition

| | |
|---|---|
| Methanol extracts of Radix Clematidis | 500.0 mg |
| Isomerized sugar | 20.0 g |
| Antioxidant | 5.0 mg |
| Methyl para-oxybenzoate | 2.0 mg |

Add purified water to make the total volume up to 100.0 ml.

4-3. Solution Composition

| | |
|---|---|
| Water extracts of Radix Clematidis | 500.0 mg |
| Isomerized sugar | 20.0 g |
| Antioxidant | 5.0 mg |
| Methyl para-oxybenzoate | 2.0 mg |

Add purified water to make the total volume up to 100.0 ml

PREPARATIVE EXAMPLE 5

Powder

Powder was prepared by mixing the following ingredients according to a general preparation, prior to putting the mixture into a bag to be sealed.

5-1. Powder Composition

| | |
|---|---|
| Petroleum ether extracts of Radix Clematidis | 50.0 mg |
| Lactose | 100.0 mg |
| Talc | 5.0 mg |

5-2. Powder Composition

| | |
|---|---|
| Methanol extracts of Radix Clematidis | 50.0 mg |
| Lactose | 100.0 mg |
| Talc | 5.0 mg |

5-3. Powder Composition

| | |
|---|---|
| Water extracts of Radix Clematidis | 50.0 mg |
| Lactose | 100.0 mg |
| Talc | 5.0 mg |

PREPARATIVE EXAMPLE 6

Injection

Injection was prepared by filling an ample of 2.0 ml with the following ingredients to be sterilized according to a general preparation.

6-1. Injection Composition

| | |
|---|---|
| Petroleum ether extracts of Radix Clematidis | 50.0 mg |
| Antioxidant | 1.0 mg |
| Tween 80 | 1.0 mg |

Add distilled water for injection to make the total volume up to 2.0 ml 6-2. Injection Composition

| | |
|---|---|
| Methanol extracts of Radix Clematidis | 50.0 mg |
| Antioxidant | 1.0 mg |
| Tween 80 | 1.0 mg |

Add distilled water for injection to make the total volume up to 2.0 ml 6-3. Injection Composition

| | |
|---|---|
| Water extracts of Radix Clematidis | 50.0 mg |
| Antioxidant | 1.0 mg |
| Tween 80 | 1.0 mg |

Add distilled water for injection to make the total volume up to 2.0 ml

PREPARATIVE EXAMPLE 7

Preparation of Natural Foods

Brown rice, barley, sweet rice, and Job's tears were gelatinized and dried, prior to roasting the dried cereals to make powder with particle size of 60 mesh using a crusher according to a known method. Black soybeans, black sesame, and perilla also were steamed and dried, prior to roasting the dried seeds to make powder with particle size of 60 mesh using a crusher according to a known method. The above-prepared cereals, seeds, and dry extracts of Radix *Clematidis* were blended in the following ratio to make granules.

7-1. Preparative Example of Natural Foods cereals: brown rice 30 wt %, Job's tears 15 wt %, barley 20 wt %, sweet rice 9 wt % seeds: perilla 7 wt %, black soybeans 8 wt %, black sesame 7 wt %, dry powder of petroleum ether extracts of Radix *Clematidis:* 3 wt %, Ling chiu mushrooms 0.5 wt %, Rehmanniae Radix 0.5 wt %

7-2. Preparative Example of Natural Foods cereals: brown rice 30 wt %, Job's tears 15 wt %, barley 20 wt %, sweet rice 9 wt % seeds: perilla 7 wt %, black soybeans 8 wt %, black sesame 7 wt %, dry powder of methanol extracts of Radix *Clematidis:* 3 wt %, Ling chiu mushrooms 0.5 wt %, Rehmanniae Radix 0.5 wt %

7-3. Preparative Example of Natural Foods cereals: brown rice 30 wt %, Job's tears 15 wt %, barley 20 wt %, sweet rice 9 wt % seeds: perilla 7 wt %, black soybeans 8 wt %, black sesame 7 wt %, dry powder of water extracts of Radix *Clematidis:* 3 wt %, Ling chiu mushrooms 0.5 wt %, Rehmanniae Radix 0.5 wt %

A composition containing extracts of Radix *Clematidis* has an effect of preventing and treating diabetes, diabetic complications, insulin resistance and insulin resistance syndrome, and can be widely used for diabetic patients.

The foregoing embodiment and advantages are merely exemplary and are not to be construed as limiting the present invention. The present teaching can be readily applied to other types of apparatuses. Also, the description of the embodiments of the present invention is intended to be illustrative, and not to limit the scope of the claims, and many alternatives, modifications, and variations will be apparent to those skilled in the art.

What is claimed is:

1. A pharmaceutical composition consisting essentially of extracts of Radix *Clematidis* for treating and reducing the risk of diabetes, loss of eyesight due to diabetes, renal failure due to diabetes, heart disease due to diabetes, insulin resistance and insulin resistance syndrome;

wherein the extracts are obtained by a method consisting essentially of extracting Radix *Clematidis* with a solvent selected from a group consisting of petroleum ether, benzene, n-hexane, toluene, and heptane.

2. The pharmaceutical composition of claim 1, wherein the extracts of Radix *Clematidis* are present in an amount between about 0.5 wt % and about 50 wt % based on the total composition weight.

3. The pharmaceutical composition of claim 1, wherein said pharmaceutical composition further consists of at least one pharmaceutically acceptable carrier.

4. The pharmaceutical composition of claim 1, wherein said pharmaceutical composition is formulated in the form of an oral formulation, external application, suppository or sterile injection.

5. The pharmaceutical composition according to claim 1, wherein said pharmaceutical composition is formulated as a food.

6. The pharmaceutical composition of claim 5, wherein the extracts of Radix *Clematidis* are present in an amount of between about 0.1 wt % and about 15 wt % based on the total food weight.

7. The pharmaceutical composition according to claim 1, wherein said pharmaceutical composition is formulated as a beverage.

8. The pharmaceutical composition of claim 7, wherein the extracts of Radix *Clematidis* are present in an amount between about 1 g and about 30 g based on a 100 mL beverage.

9. A pharmaceutical composition consisting essentially of extracts of Radix *Clematidis* for treating and reducing the risk of diabetes, loss of eyesight due to diabetes, renal failure due to diabetes, heart disease due to diabetes, insulin resistance and insulin resistance syndrome;

wherein the extracts are obtained by a method consisting essentially of:

extracting Radix *Clematidis* with petroleum ether;

removing the resulting petroleum ether extract fraction; and extracting the remaining Radix *Clematidis* residue with a second solvent selected from a group consisting of C1-4 lower alcohol, a mixture of the lower alcohol and water, acetone, chloroform, methylene chloride, ether, and ethylacetate.

10. A pharmaceutical composition consisting essentially of extracts of Radix *Clematidis* for treating and reducing the risk of diabetes, loss of eyesight due to diabetes, renal failure due to diabetes, heart disease due to diabetes, insulin resistance and insulin resistance syndrome;

wherein the extracts are obtained by a method consisting essentially of:

extracting Radix *Clematidis* with petroleum ether;

removing the resulting petroleum ether extract fraction;

extracting the remaining Radix *Clematidis* residue with a second solvent selected from a group consisting of C1-4 lower alcohol, a mixture of the lower alcohol and water, acetone, chloroform, methylene chloride, ether, and ethylacetate;

removing the resulting solvent extract fraction; and extracting the remaining residues of Radix *Clematidis* with water.

* * * * *